(12) United States Patent
Dekker et al.

(10) Patent No.: US 10,736,607 B2
(45) Date of Patent: Aug. 11, 2020

(54) INTEGRATED CIRCUIT ARRAY AND METHOD FOR MANUFACTURING AN ARRAY OF INTEGRATED CIRCUITS

(71) Applicant: KONINKLIJKE PHILIPS N.V., Eindhoven (NL)

(72) Inventors: Ronald Dekker, Eindhoven (NL); Vincent Adrianus Henneken, Eindhoven (NL); Angel Metodiev Savov, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1123 days.

(21) Appl. No.: 15/035,779

(22) PCT Filed: Oct. 16, 2014

(86) PCT No.: PCT/EP2014/072260
§ 371 (c)(1),
(2) Date: May 11, 2016

(87) PCT Pub. No.: WO2015/071051
PCT Pub. Date: May 21, 2015

(65) Prior Publication Data
US 2016/0256133 A1 Sep. 8, 2016

(30) Foreign Application Priority Data
Nov. 15, 2013 (EP) ...................... 13193066

(51) Int. Cl.
*A61B 8/14* (2006.01)
*A61B 8/00* (2006.01)
(Continued)

(52) U.S. Cl.
CPC ............. *A61B 8/4494* (2013.01); *A61B 8/12* (2013.01); *H01L 23/5386* (2013.01);
(Continued)

(58) Field of Classification Search
None
See application file for complete search history.

(56) References Cited

U.S. PATENT DOCUMENTS

2006/0255433 A1 11/2006 Xu
2007/0013269 A1* 1/2007 Huang ................. B06B 1/0292
310/334
(Continued)

FOREIGN PATENT DOCUMENTS

EP 1883107 A2 1/2008
JP 2011166633 A 8/2011
(Continued)

OTHER PUBLICATIONS

Zhuang, et al., "Biocompatible coating for CMUTs in a harsh, aqueous environment", Journal of Micromechanics and Microengineering, Apr. 17, 2007, pp. 994-1001.
(Continued)

*Primary Examiner* — Joel F Brutus (57) ABSTRACT

An integrated circuit array, in particular for two dimensional sensor arrays such as ultrasound imaging systems is disclosed. The integrated circuit array (10) comprises a plurality of integrated circuit elements (12) each formed in a substrate (14), wherein the substrates are separated from each other. The array comprises a flexible and/or stretchable connection layer (22) connected to the integrated circuit elements for flexibly connecting the integrated circuit elements to each other. The array further comprises a plurality of electrical interconnects (18) for electrically connecting the integrated circuit elements to each other, wherein the electrical interconnects are formed as metal lines in one piece with integrated interconnects of the integrated circuit elements.

9 Claims, 6 Drawing Sheets

(51) Int. Cl.
  *H01L 23/538*   (2006.01)
  *H01L 23/00*    (2006.01)
  *A61B 8/12*     (2006.01)
  *H01L 25/04*    (2014.01)

(52) U.S. Cl.
  CPC .......... *H01L 23/5387* (2013.01); *H01L 24/24* (2013.01); *H01L 24/82* (2013.01); *H01L 24/94* (2013.01); *H01L 25/042* (2013.01); *A61B 2562/0204* (2013.01); *H01L 2224/24137* (2013.01); *H01L 2224/94* (2013.01); *H01L 2924/10253* (2013.01); *H01L 2924/14* (2013.01)

(56) References Cited

U.S. PATENT DOCUMENTS

| | | | |
|---|---|---|---|
| 2008/0273424 A1* | 11/2008 | Wodnicki | A61B 8/0833 367/180 |
| 2010/0255623 A1* | 10/2010 | Huang | B06B 1/0292 438/51 |
| 2010/0262014 A1 | 10/2010 | Huang | |
| 2011/0071397 A1* | 3/2011 | Wodnicki | B06B 1/0629 600/459 |
| 2011/0136284 A1 | 6/2011 | Huang | |

FOREIGN PATENT DOCUMENTS

| | | |
|---|---|---|
| WO | 9832595 A1 | 7/1998 |
| WO | 2009073753 A1 | 6/2009 |
| WO | 2012066477 A1 | 5/2012 |

OTHER PUBLICATIONS

Chen, "Topical Review; Capacitive micromachined ultrasonic transducer arrays for minimally invasive medical ultrasound", Journal of Micromechanics & Microengineering, Institute of Physics Publishing, vol. 20, No. 2, Jan. 29, 2010.

Ergun, et al., "Capacitive Micromachined Ultrasonic Transducers: Fabrication Technology", IEEE Transactions of Ultrasonics, Ferroelectrics, and Frequency Control, vol. 52, No. 12, Dec. 2005, pp. 2242-2258.

* cited by examiner

INTEGRATED CIRCUIT ARRAY AND METHOD FOR MANUFACTURING AN ARRAY OF INTEGRATED CIRCUITS

This application is the U.S. National Phase application under 35 U.S.C. § 371 of International Application No. PCT/EP2014/072260, filed on Oct. 16, 2014, which claims the benefit of European Patent Application No. 13193066.1, filed Nov. 15, 2013. These applications are hereby incorporated by reference herein.

FIELD OF THE INVENTION

The present invention relates to an integrated circuit array, in particular for two dimensional sensor arrays such as ultrasound imaging systems and to a method of manufacturing a corresponding array of integrated circuits. The present invention relates further to an ultrasound transducer, for example for intravascular ultrasound systems.

BACKGROUND OF THE INVENTION

In the field of two dimensional sensor arrays it is generally known to connect circuits and sensors by means of bendable and/or stretchable electrical interconnects in order to provide flexible and/or stretchable sensor arrays. Such stretchable and/or bendable circuits and sensors are of growing importance in the field of bio-medical systems since they can be formed or shaped in such a way that they match with the human body such as cylindrical intravascular ultrasound transducer or implant sensor arrays such as retinal implant optical sensors.

In the field of minimal-invasive medical instruments, flexible and stretchable circuits are important to form high performance sensor systems like imaging systems which can be attached to cylindrical or spherical instruments. For stretchable capacitive micromachined ultrasound transducer (CMUT) arrays, the rigid chips are thinned and bent around the instruments, which causes mechanical stress within the transducer arrays. For manufacturing a stretchable CMUT array, the individual transducer elements are usually fabricated on a silicon wafer and attached to a flexible layer or foil and separated from each other by an etching process. The individual sensor devices are usually electrically connected to each other by means of electrical interconnects connected to each of the sensor devices in a separate process step. A corresponding capacitive micromachined ultrasound transducer array for a catheter is e.g. known from WO 2012/066477 A1.

The disadvantage of the known circuit arrays and sensor arrays is that the connection of the electrical interconnects during a post-processing step is complicated so that a technical effort for manufacturing the circuit arrays and/or sensor arrays is increased.

From WO 9832595 a flexible skin is known incorporating microelectromechanical devices, wherein the flexible skin comprises silicon islands encapsulated in a polyimide film, wherein the silicon islands are formed by etching silicon wafers to a desirable thickness by wet etching and pattering from the back side by reactive ion etching.

From US 2006/0255433 A1 a semiconductor-containing flexible skin is known which is suitable for use in intelligent textile applications including a metal layer, an insulating layer and one or more semiconductor islands sandwiched between a first flexible polymer layer and a second flexible polymer layer.

From J. Chen: "Topical Review; Capacitive micromachined ultrasonic transducer arrays for minimally invasive medical ultrasound" in Journal of Micromechanics and Microengineering, Vol. 20, No. 2, 1 Feb. 2010, page 23001 an assembly of a planar monolithic CMUT-array is known, wherein imager plates are connected to each other by flexible dielectric membranes fabricated monolithically with the transducer. From EP 1 883 107 A2 a packaged microelectronic device is known comprising at least one electrode comprising a chip embedded in a package, wherein the chips are connected to each other by flexible electrical interconnects.

SUMMARY OF THE INVENTION

It is an object of the present invention to provide an improved flexible or stretchable integrated circuit array, which can be manufactured with low technical effort. It is further an object of the present invention to provide an improved method for manufacturing a flexible and/or stretchable array of integrated circuits with low technical effort. It is finally an object of the present invention to provide a flexible and/or stretchable ultrasound transducer assembly which can be manufactured with low technical effort.

In a first aspect of the present invention, an integrated circuit array, in particular for two dimensional sensor arrays such as ultrasound imaging systems is provided, comprising:
  a plurality of integrated circuit elements each formed in a substrate portion, wherein the substrate portions are separated from each other,
  a flexible and/or stretchable connection layer coupled to the integrated circuit elements for flexibly connecting the integrated circuit elements to each other, and
  a plurality of electrical interconnects for electrically coupling the integrated circuit elements to each other, wherein the electrical interconnects are formed as metal lines in one piece with integrated interconnects of the integrated circuit elements.

In a further aspect of the present invention, a method for manufacturing an array of integrated circuits, in particular for two-dimensional sensor arrays such as ultrasound imaging systems is provided, comprising the steps of:
  providing a substrate including a plurality of integrated circuit elements electrically coupled to each other by means of electrical interconnects formed as integrated metal lines,
  exposing the electrical interconnects,
  coupling a flexible and/or stretchable connection layer to the integrated circuit elements separately from the electrical interconnects to provide a flexible connection between the integrated circuit elements, and
  mechanically separating substrate portions including the integrated circuit elements from each other such that the integrated circuit elements are flexibly connected by means of the flexible connection layer.

In a still further aspects of the present invention, an ultrasound transducer, e.g. for intravascular ultrasound systems is provided comprising a transducer array including a plurality of ultrasound transducer elements for emitting and/or receiving ultrasound waves, and an integrated circuit array according to the present invention for driving the transducer elements.

Preferred embodiments of the inventions are defined in the dependent claims. It should be understood that the claimed method has similar and/or identical preferred embodiments as the claimed device and as defined in the dependent claims.

The present invention is based on the idea to use integrated interconnects for electrically connecting the separated integrated circuits to each other for connecting the integrated circuits flexibly to each other. The integrated interconnects are formed as integrated metal lines together with the integrated circuits in an IC process and are exposed when the substrate portions are separated from each other. Since the electrical interconnects are already processed during the IC process, the electrical connection of the integrated circuits in a post-process after connecting to the flexible connection layer can be omitted. Hence, the manufacturing effort for manufacturing the integrated circuit array can be reduced. According to the present invention, the term flexible means that the integrated circuits are movable with respect to each other in any direction, e.g. may be bendable and/or stretchable with respect to each other. The electrical interconnects may be exposed partially or entirely during the manufacturing process.

In a preferred embodiment, the electrical interconnects are separated from the connection layer. This is a possibility to form a bendable and stretchable electrical connection between the integrated circuit elements with low technical effort.

In a preferred embodiment, the electrical interconnects are electrically isolated from each other by means of an isolation layer. This is a simple possibility to provide a plurality of electrical interconnects with a low distance to each other while assuring the electrical function of the integrated circuit elements.

In a further preferred embodiment, the isolation layer comprises a parylene layer. This is a possibility to apply a uniform pin hole-free isolation layer to the electrical interconnects with low technical effort and which is further biocompatible so that the integrated circuit array can be used for medical applications.

In a further embodiment, the isolation layer is a layer deposited by atomic layer deposition.

In a preferred embodiment, the integrated circuit elements are each connected to a sensor element for detecting measurement values. This is a simple possibility to provide two dimensional measurement arrays with low dimensions, e.g. for intravascular applications, since the integrated circuit elements can be utilized for driving the sensor elements and for evaluating the detected measurement values.

In a further preferred embodiment, the sensor elements are ultrasound transducer elements for emitting and/or receiving ultrasound waves. This is a possibility to provide a flexible and/or stretchable ultrasound transducer array e.g. for intravascular ultrasound systems, which can be adapted to e.g. cylindrical or spherical instruments.

In a further preferred embodiment, the electrical interconnects are formed as sub-micron metal lines. This is a possibility to realize a high speed or large volume data connection between the integrated circuit elements with a reduced size, since many parallel metal lines can be connected between the integrated circuit elements.

In a preferred embodiment, the electrical interconnects have in a top view at least section-wise a curved shape for flexible and/or stretchable connecting the integrated circuit elements to each other. This is a possibility to achieve a bendable or stretchable electrical connection between the integrated circuit elements so that the integrated circuit array can be applied with high flexibility to different surfaces.

In a preferred embodiment, the electrical interconnects are formed in a plurality of levels disposed above each other, wherein the electrical interconnects of the different levels are at least partially mechanically connected to each other by an isolation layer, in particular by means of an oxide layer. The electrical interconnects may be connected to each other sectionwise so that the isolation layer form pillars between the electrical interconnects. This is a possibility to increase the mechanical stability of the electrical interconnects.

In a preferred embodiment of the method, the electrical interconnects are coated by means of an isolation layer comprising parylene. This is a possibility to isolate the electrical interconnect from each other with a reliable pin hole-free layer with low technical effort which is biocompatible so that the integrated circuit array can be used for medical applications.

In a further preferred embodiment of the method the interconnects are embedded or overmolded by means of a removable protection mold prior to the connecting of the flexible connection layer. This is a possibility to avoid that the electrical interconnects are integrated or attached to the flexible and/or stretchable connection layer so that a reliable manufacturing method of the integrated circuit array can be provided.

In a preferred embodiment, the protection mold is removed to expose the electrical interconnects. This is a possibility to provide free standing electrical interconnects which can be stretched and bended so that a reliable flexible integrated circuit array can be provided.

In a preferred embodiment, the method further comprises the step of connecting sensor elements to each of the integrated circuit elements for detecting measurement values. This is a possibility to provide a two-dimensional sensor array with a reduced size, since the integrated circuit elements can be used for driving the sensor elements and for evaluating the measurement values.

In a preferred embodiment, the sensor elements are ultrasound transducer elements for emitting and/or receiving ultrasound waves. This is a possibility to provide a flexible or stretchable ultrasound transducer array.

It is further preferred if the integrated circuits are mechanically separated from each other by disconnecting the substrate portions at positions corresponding to the positions of the exposed interconnects. This is a simple possibility to disconnect the integrated circuit elements from each other and to provide a flexible two dimensional array of integrated circuits.

As mentioned above, due to the electrical connection of the integrated circuit element by means of electrical interconnects, which are produced during the integrated circuit process of the integrated circuit elements in one piece with the integrated interconnects of the integrated circuit elements, the electrical interconnects can be manufactured with low technical effort in advance of attaching the flexible connection layer so that the overall technical effort for manufacturing flexible arrays of integrated circuit can be reduced.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
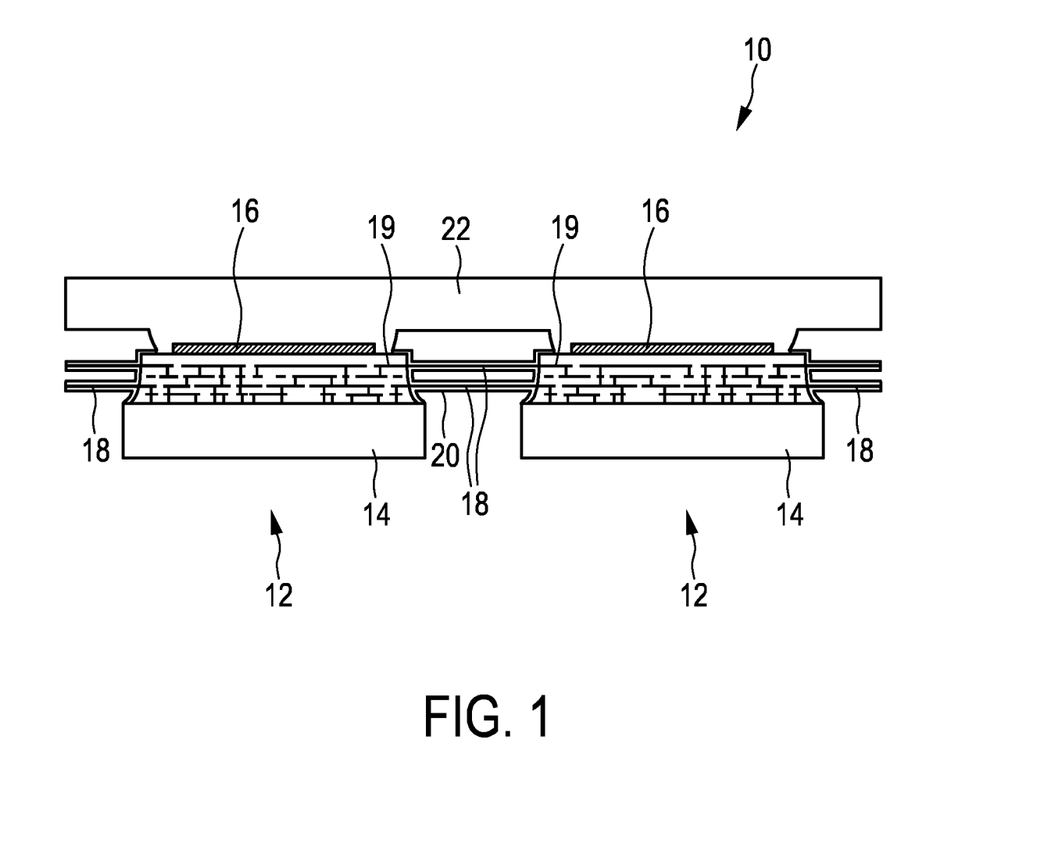
FIG. 1 shows a schematic sectional view of a flexible integrated circuit array.

FIG. 1 shows a schematic sectional view of a flexible integrated circuit array generally denoted by 10. The integrated circuit array 10 includes a plurality of integrated circuit elements 12 each formed in a substrate 14. The integrated circuit elements 12 are each connected to a sensor device 16 which is in a certain embodiment formed as an ultrasound transducer element 16 such as a capacitive micromachined ultrasound transducer (CMUT) element. The integrated circuit elements 12 comprise integrated circuits in multiple layers formed during CMOS fabrication. The integrated circuits are formed by an integrated circuit process within the silicon substrate 14. The substrates 14 of the integrated circuit elements are separated from each other, wherein the integrated circuit elements 12 or the integrated circuits of the integrated circuit elements 12 are electrically connected to each other by means of a plurality of electrical interconnects 18. The electrical interconnects 18 are metal lines and formed during the integrated circuit fabrication process together with integrated electrical interconnects 19 of the integrated circuit elements 12 and, therefore, formed monolithically in one piece with the integrated electrical interconnects 19. The electrical interconnects 18 are covered by means of an isolation layer 20, which is formed as a parylene layer. The parylene is a coating, which is applied by chemical vapor deposition (CVD) at low pressure and at room temperature. Parylene provides a conformal deposition and is a pin hole-free layer and can be formed having a thickness of 50-100 nm. Parylene is further biocompatible so that this material can be used for medical application and in particular for long-term implants.

The electrical interconnects 18 are formed as electrical metal interconnects during the manufacturing process of the integrated metal lines of the integrated circuit elements 12 and exposed by means of an etch process as described in the following so that the electrical interconnects 18 are free standing electrical connections between the integrated circuit elements 12. The electrical interconnects 18 have in a top view a meander shape or a horse-shoe shape so that the electrical interconnects 18 are easily bendable or stretchable. The electrical interconnects 18 are preferably sub-micron interconnects formed in multiple layers so that a data connection can be provided for submitting a large volume of data, e.g. image data such as a bus line. The electrical interconnects 18 may also serve for providing electrical power to the integrated circuit elements 12.

The integrated circuit elements 12 are connected to a flexible connection layer 22, which is preferably formed by a polydimethylsiloxane (PDMS) layer for flexible connecting the integrated circuit elements 12 to each other.

Since the substrates 14 are mechanically separated from each other or in other words since the integrated circuit elements 12 have no rigid connection and since the flexible connection layer 22 is connected to the integrated circuit elements 12, the integrated circuit array 10 can be provided as a two dimensional flexible array of integrated circuit elements 12. Since the electrical interconnects 18 are bendable and stretchable, the flexible integrated circuit array 10 can be formed and deformed in almost any shape e.g. to cover cylindrical or spherical surfaces, e.g. of intravascular sensors or endoscopes. Since the sensor elements 16 are directly contacted to the integrated circuit elements 12, the sensor elements 16 can be driven by means of the integrated circuit elements 12 and the measurement values provided by the sensor elements 16 can be directly evaluated and transmitted via the electrical interconnects 18 so that a two dimensional sensor array can be provided with small dimensions.

In a preferred embodiment, the sensor elements 16 are formed as capacitive micromachined transducer elements for emitting and receiving ultrasound waves, so that a flexible ultrasound image sensor array can be provided with small dimensions e.g. for intravascular sensor applications. In an alternative embodiment, the sensor elements 16 are optical sensors, e.g. photo diodes for providing an imaging array.

Figure 2:
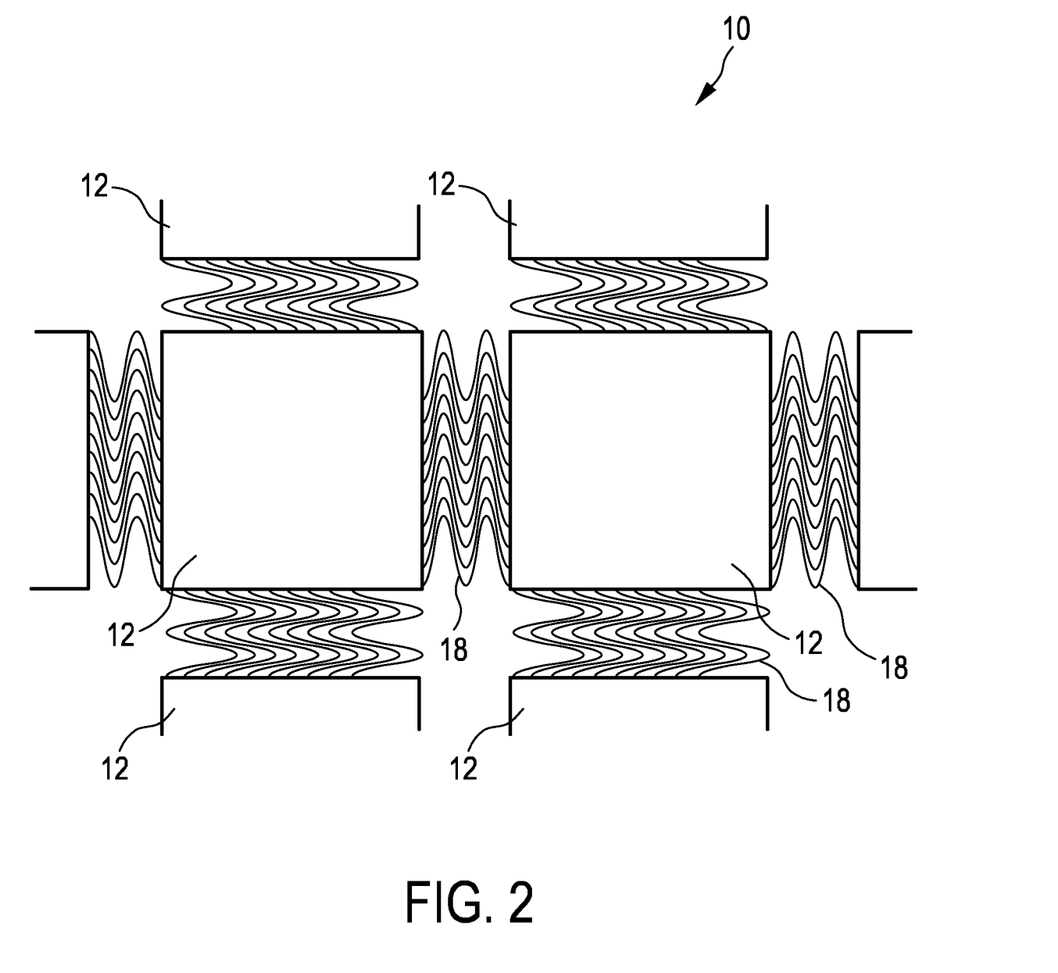
FIG. 2 shows a sectional top view of the flexible integrated circuit array shown in FIG. 1.

In FIG. 2 a sectional top view of the integrated circuit array 10 shown in FIG. 1 is schematically shown. Identical elements are denoted by identical reference numerals, wherein here merely the differences are described in detail.

The integrated circuit elements 12 are connected to each other via the electrical interconnects 18, which have a meander shape so that the electrical interconnects 18 can be bent and stretched so that the integrated circuit array 10 can be covered to almost any non-flat surface and a flexible use of the integrated circuit array 10 is possible.

The integrated circuit array 10 is formed as a two dimensional array as shown in FIG. 2, wherein each inner integrated circuit element 12 is connected to four surrounding integrated circuit elements 12. It shall be understood that the integrated circuit elements 12 at an edge of the integrated circuit array 10 are merely connected to three integrated circuit elements 12 and the corner integrated circuit elements 12 are connected merely to two surrounding integrated circuit elements 12. The integrated circuit array 10 may be formed of a smaller or larger amount of connected adjacent integrated circuit elements 12, e.g. a hexagonal array. In general, the shape, size and/or distribution of the elements is not limited to embodiments shown in the figures.

FIG. 3a-i shows a sequence of manufacturing steps for manufacturing the integrated circuit array 10. Identical elements are denoted by identical reference numerals, wherein here merely the differences are disclosed in detail.

Figure 3A:
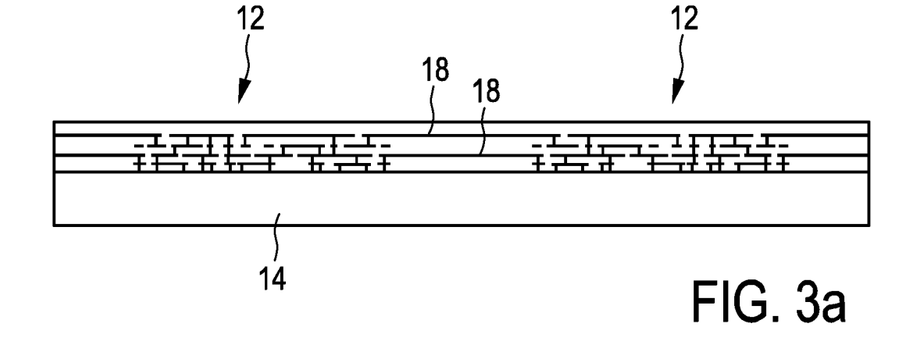
FIGS. 3a-i show a sequence of manufacturing steps for manufacturing the flexible integrated circuit array of FIG. 1.

In FIG. 3a the starting point of the method is shown, wherein a fully fabricated IC wafer is provided. The integrated circuit elements 12 are integrated in the substrate 14 which is still formed as one piece. The integrated circuit elements 12 comprise different circuit layers, wherein the integrated circuit elements 12 are electrically connected by means of the electrical interconnects 18, which are at this stage of the process still integrated in the silicon wafer. The silicon wafer at this starting point may be provided with the sensor elements 16 which may be connected to each of the integrated circuit elements 12, wherein the sensor elements 16 are not shown in FIG. 3.

Figure 3B:
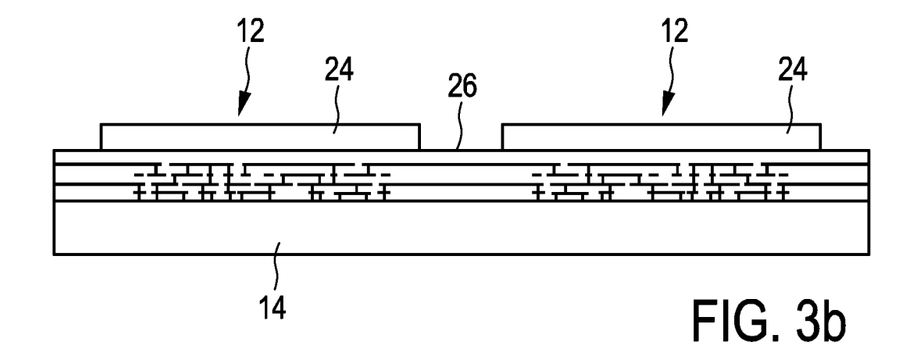

In a following step shown in FIG. 3b, a resist layer 24 such as a photoresist or a hard mask layer is applied to a surface 26 of the silicon wafer. The resist layer is patterned, so that the integrated circuit elements 12 are covered by the resist layer 24 and the portions of the surface 26 between the integrated circuit elements 12 above the electrical interconnects 18 are exposed.

Figure 3C:
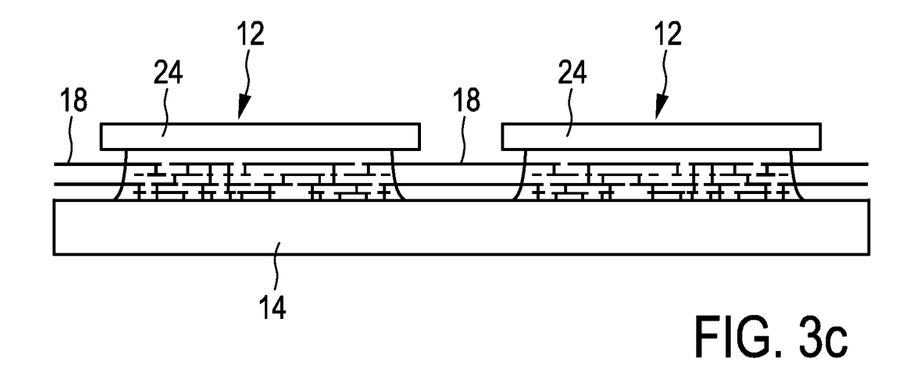

In a following step shown in FIG. 3c, oxide which forms an intermetal dielectric surrounding the electrical interconnects 18 is etched so that the electrical interconnects 18 are exposed. The etch process is preferably an isotropic etch process so that the electrical interconnects 18 are entirely exposed and all intermetal dielectric is removed. In an alternative embodiment, the oxide is partially removed so that the electrical interconnects 18 are partially exposed so that the electrical interconnects 18 are partially connected to each other by remaining oxide layers. This may be performed by means of a dry etch process. The dry etch process may be a reactive ion etch (RIE) which etches oxide selectively with respect to aluminum of the electrical interconnect 18. An example of a suitable wet etch is an etch liquid composed of one part acidic acid and two parts ammonium fluoride. An example for a suitable RIE etch is a CF4-based chemistry.

Figure 3D:
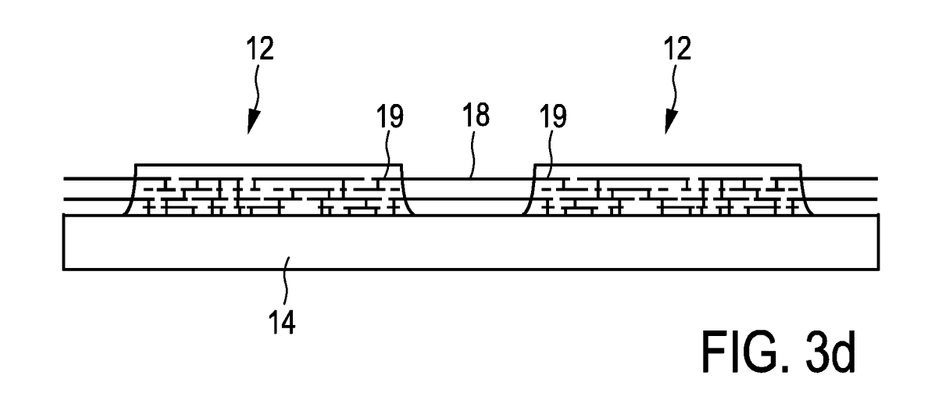

After the etch process, the resist layer 24 is removed as shown in FIG. 3d. Because of the small dimensions and the small weight of the electrical interconnects 18, the electrical interconnects 18 remains suspended without bending over distances of tens of microns.

Figure 3E:
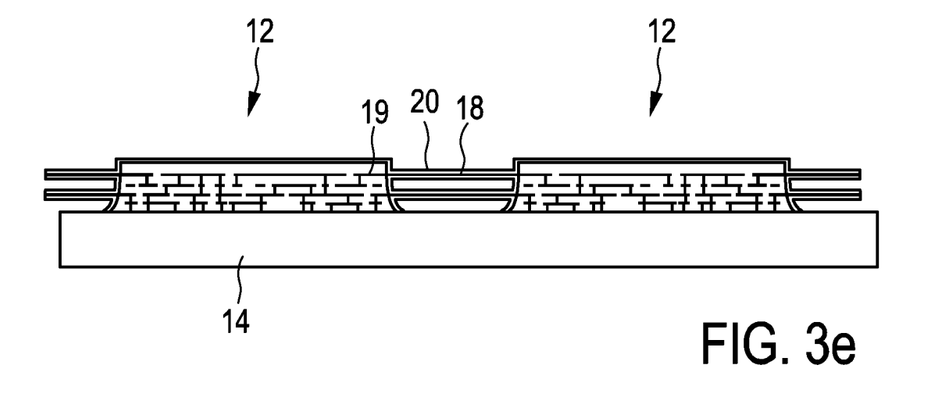

In FIG. 3e the isolation layer 20 is deposited on the whole silicon wafer, wherein the isolation layer is formed of a parylene layer, which is a coating applied by chemical vapor deposition (CVD) at low pressure and at room temperature. The parylene layer exhibits a conformal deposition growing on any and around every exposed structure so that the electrical interconnects 18 are entirely covered and/or isolated by means of the parylene layer. Further, the parylene is pin hole-free for layers down to 50-100 nm. Finally, the parylene layer is biocompatible so that the so coated elements can be used for medical applications and also for long-term implants.

Figure 3F:
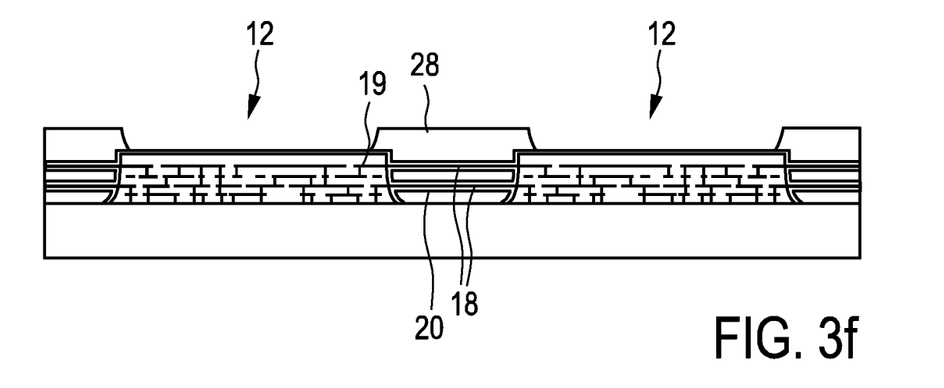

In a following step shown in FIG. 3f, temporary resist structures 28 are formed between the integrated circuit elements 12 so as to protect the isolated electrical interconnects 18 for the following process steps. The resist may be a photo resist and can be applied by spin coating or spray coating, wherein the resist 28 is patterned e.g. by means of a photolithography and developing process so as to expose the surface of the integrated circuit elements 12.

Figure 3G:
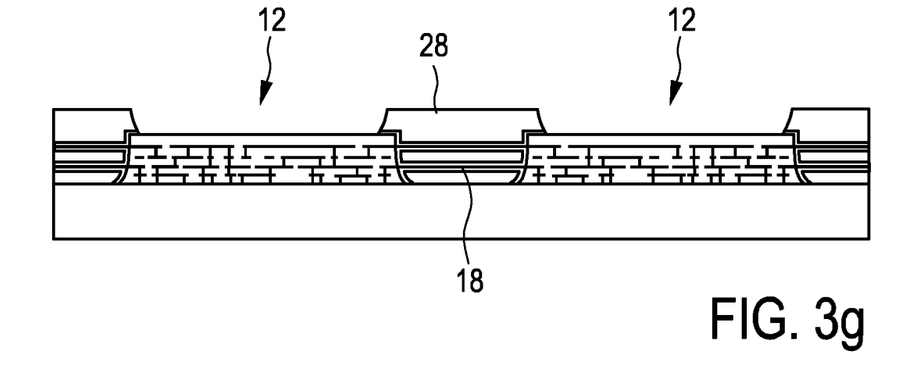

In a following step shown in FIG. 3g, the isolation layer 20 covering the surface of the integrated circuit element is removed since the adhesion of PDMS to the parylene layer is low comparable to the adhesion of PDMS to silicon oxide.

Figure 3H:
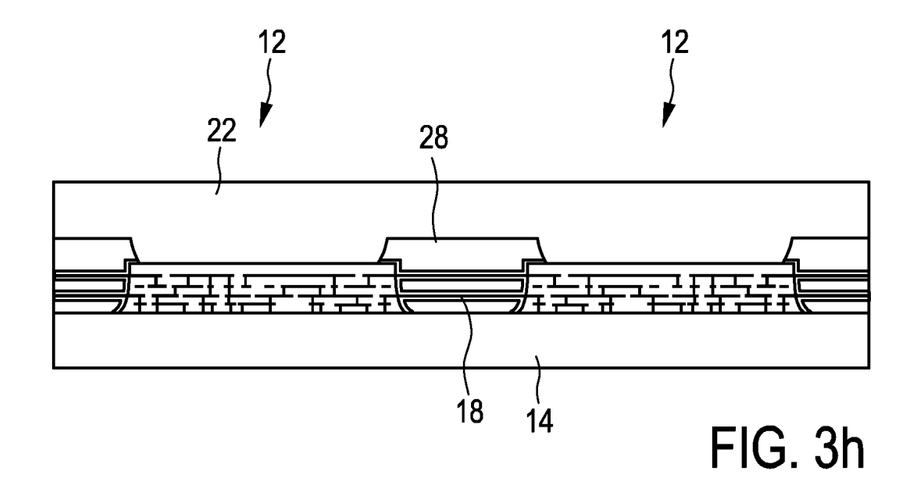

In a following step shown in FIG. 3h, the polydimethylsiloxane layer (PDMS) is applied to the surface of the silicone wafer so as to form the flexible connection layer 22 for flexibly connecting the integrated circuit elements 12. The PDMS layer is preferably applied by spin-coating or spray-coating or molding depending on the required layer thickness.

Figure 3I:
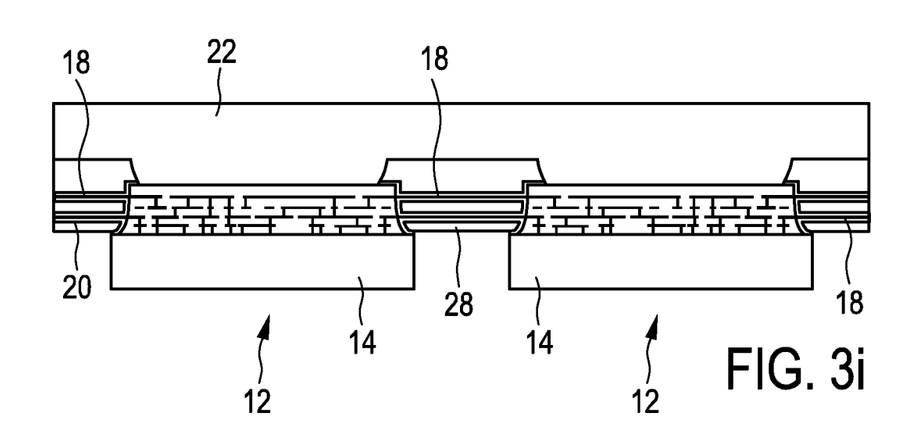

In a following step shown in FIG. 3i, the substrate 14 between the integrated circuit elements 12 or the portion of the substrate 14 rigidly connecting the integrated circuit elements 12 to each other below the electrical interconnects 18 and the resist 28 is removed by means of an etching process preferably by means of a deep reactive ion etching (DRIE), which stops on the resist layer 28 surrounding the electrical interconnects 18.

In a final step, the resist layer 28 is removed by a solvent, e.g. by acetone or a developer, so that the isolated electrical interconnects 18 are free standing and the integrated circuit elements 12 are merely flexibly connected to each other by means of the flexible connection layer 22 as shown in FIG. 1.

Conclusively, since the integrated circuit elements 12 are connected via the electrical interconnect, which are formed during the integrated circuit process as integrated metal lines and, therefore, formed monolithically in one piece with the integrated electrical interconnects 19 of the integrated circuit elements 12 and exposed during the following steps, the electrical connection between the integrated circuit element 12 can be achieved with low technical effort.

Figure 4A:
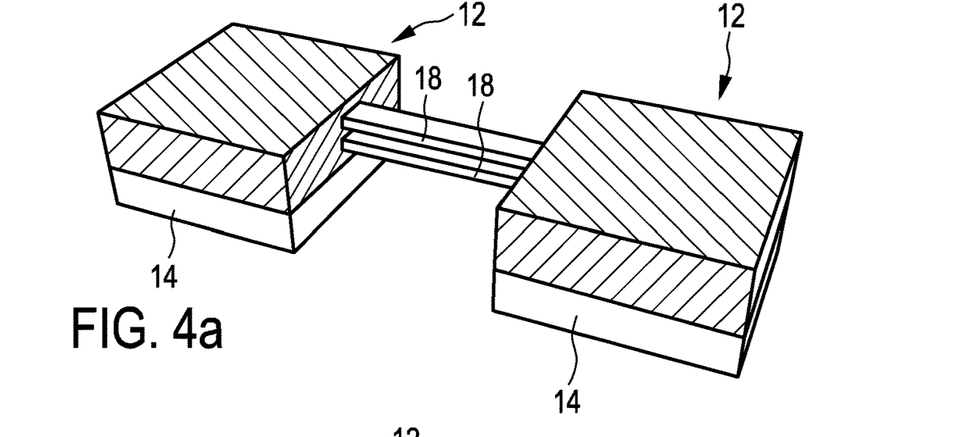
FIGS. 4a-c show different embodiments of exposed electrical interconnects in a schematic perspective view.
Figure 4B:
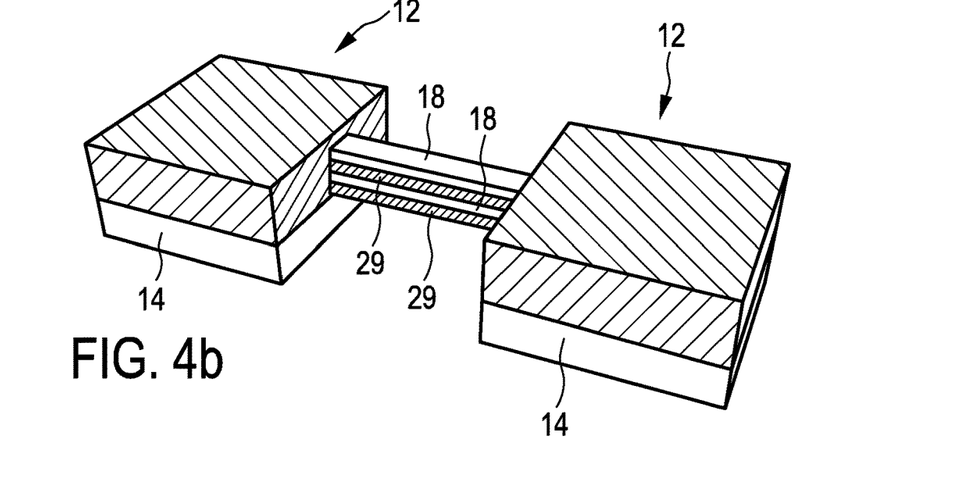
Figure 4C:
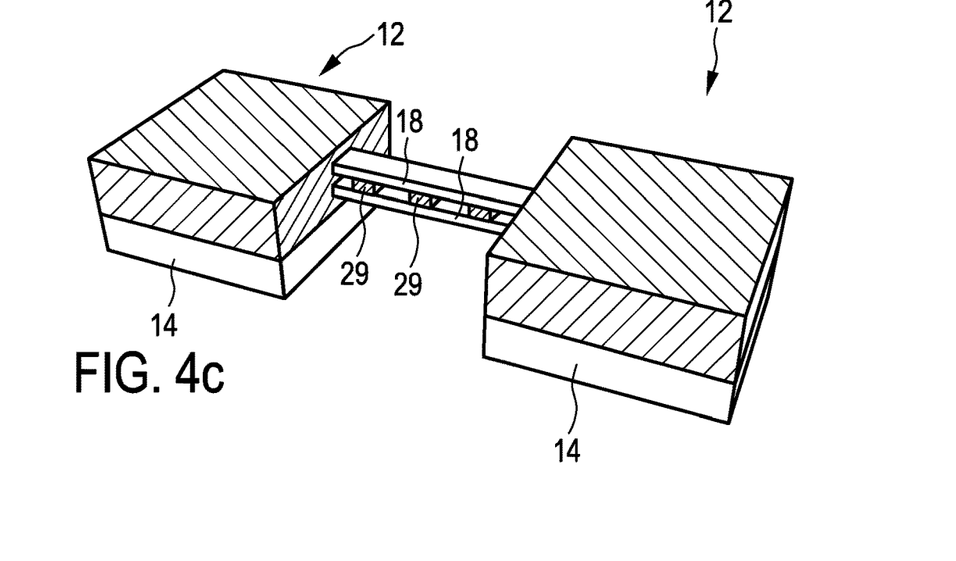

FIGS. 4a-c show different embodiments of exposed electrical interconnects in a schematic perspective view. Identical elements are denoted by identical reference numerals, wherein here merely the differences are described in detail.

In FIG. 4a the electrical interconnects 18 are disposed above each other and entirely exposed, i.e. the oxide is entirely removed e.g. by means of the wet etch process or an isotropic dry etch process. The electrical interconnects 18 form a stack of interconnects or multilevel interconnects.

In FIG. 4b the oxide above and beside the electrical interconnects 18 is removed, wherein intermetal oxide layers 29 between the electrical interconnects 18 and below the electrical interconnects 18 are preserved. These intermetal oxide layers 29 can prevent short circuits between the electrical interconnects 18 and provide an increased mechanical stability of the electrical interconnects 18. These intermetal oxide layers 29 can be manufactured by means of a dry etch process like reactive ion etching (RIE).

In FIG. 4c the intermetal oxide layers 29 between the electrical interconnects 18 are partially or sectionwise removed so that the electrical interconnects 18 are connected to each other by pillars of oxide. These pillars can prevent short circuits between the electrical interconnects 18 and provide an increased mechanical stability of the electrical interconnects 18 while the electrical interconnects 18 are still flexible.

In FIG. 4a-c a schematic drawing of the integrated circuit array 10 is shown. For clarity reasons, the flexible connection layer 22 is not shown in FIG. 4 a-c. It shall be understood that the intermetal oxide layers 29 are also applicable for curved electrical interconnects 18 and for a more dimensional circuit array.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:
1. An integrated circuit array for ultrasound imaging systems, comprising:
  a plurality of substrate portions separated from one another,
  a plurality of integrated circuit elements respectively formed in the plurality of substrate portions such that each integrated circuit element is formed in a different substrate portion, wherein each integrated circuit element comprises a plurality of integrated metal lines,
  a flexible and/or stretchable connection layer coupled to the plurality of integrated circuit elements and config- ured for flexibly connecting the plurality of integrated circuit elements to each other, and a plurality of electrical interconnects configured for electrically coupling the plurality of integrated circuit elements to each other, wherein the plurality of electrical interconnects is formed as metal lines in one piece with the plurality of integrated metal lines of each integrated circuit element, wherein the plurality of electrical interconnects comprises a curved shape such that the plurality of electrical interconnects is stretchable.

2. The integrated circuit array as claimed in claim 1, wherein the electrical interconnects are separated from the connection layer.

3. The integrated circuit array as claimed in claim 2, wherein the electrical interconnects are electrically isolated from each other by means of an isolation layer.

4. The integrated circuit array as claimed in claim 3, wherein the isolation layer comprises a parylene layer or a layer deposited by atomic layer deposition.

5. The integrated circuit array as claimed in claim 1, wherein the integrated circuit elements are each coupled to a sensor element for detecting measurement values.

6. The integrated circuit array as claimed in claim 5, wherein the sensor elements are ultrasound transducer elements for emitting and receiving ultrasound waves.

7. The integrated circuit array as claimed in claim 1, wherein the electrical interconnects are formed as sub-micron metal lines.

8. The integrated circuit array as claimed in claim 1, wherein the integrated circuit array is incorporated into an intraluminal device.

9. The integrated circuit array as in claim 8, wherein the intraluminal device is a catheter.

* * * * *